United States Patent
Dixon et al.

(10) Patent No.: US 6,695,845 B2
(45) Date of Patent: *Feb. 24, 2004

(54) METHOD AND APPARATUS UTILIZING INTERFERENCE FIT SCREW SHANKS FOR NONMETALLIC SPINAL STABILIZATION

(76) Inventors: Robert A Dixon, 10577 Durham Pl., Powell, OH (US) 43065; Donald J Hackman, 3499 Kirkham Rd., Columbus, OH (US) 43221

( * ) Notice: Subject to any disclaimer, the term of this patent is extended or adjusted under 35 U.S.C. 154(b) by 24 days.

This patent is subject to a terminal disclaimer.

(21) Appl. No.: 09/977,663

(22) Filed: Oct. 15, 2001

(65) Prior Publication Data

US 2002/0045897 A1 Apr. 18, 2002

Related U.S. Application Data

(60) Provisional application No. 60/240,697, filed on Oct. 16, 2000.

(51) Int. Cl.[7] .............................................. A61B 17/58
(52) U.S. Cl. ........................................ 606/70; 606/61
(58) Field of Search .............................. 606/69, 70, 71, 606/61

(56) References Cited

U.S. PATENT DOCUMENTS

| | | | | |
|---|---|---|---|---|
| 2,494,229 A | * | 1/1950 | Collison | 606/73 |
| 3,593,709 A | * | 7/1971 | Halloran | 606/69 |
| 4,503,848 A | * | 3/1985 | Caspar et al. | 606/69 |
| 5,098,434 A | * | 3/1992 | Serbousek | 606/73 |
| 5,147,361 A | * | 9/1992 | Ojima et al. | 606/61 |
| 5,159,213 A | * | 10/1992 | Johnson | 606/70 |
| 5,275,601 A | | 1/1994 | Gogolewski et al. | |
| 5,364,339 A | * | 11/1994 | Carver | 602/47 |
| 5,520,690 A | * | 5/1996 | Errico et al. | 606/61 |
| 5,522,895 A | | 6/1996 | Mikos | |
| 5,578,034 A | | 11/1996 | Estes | |
| 5,676,666 A | * | 10/1997 | Oxland et al. | 606/61 |
| 5,681,310 A | * | 10/1997 | Yuan et al. | 606/61 |
| 5,681,311 A | * | 10/1997 | Foley et al. | 606/61 |
| 5,772,662 A | * | 6/1998 | Chapman et al. | 606/69 |
| 5,904,683 A | * | 5/1999 | Pohndorf et al. | 606/61 |
| 6,129,730 A | * | 10/2000 | Bono et al. | 606/73 |
| 6,159,213 A | | 12/2000 | Rogozinski | |
| 6,206,881 B1 | | 3/2001 | Frigg et al. | |
| 6,206,882 B1 | * | 3/2001 | Cohen | 606/69 |
| 6,228,085 B1 | | 5/2001 | Theken et al. | |
| 6,235,033 B1 | * | 5/2001 | Brace et al. | 606/69 |
| 6,269,716 B1 | | 8/2001 | Amis | |
| 6,293,949 B1 | * | 9/2001 | Justis et al. | 606/61 |
| 6,342,055 B1 | * | 1/2002 | Eisermann et al. | 606/69 |
| 2001/0014807 A1 | * | 8/2001 | Wagner et al. | 606/61 |
| 2002/0004660 A1 | * | 1/2002 | Henniges et al. | 606/69 |
| 2002/0016595 A1 | * | 2/2002 | Michelson | 606/73 |

FOREIGN PATENT DOCUMENTS

EP 0530585 10/1993

OTHER PUBLICATIONS

Macro Pore Resorbable Technology Insructional Guide, 2000, MacroPore Inc., San Diego California, (brochure).

* cited by examiner

Primary Examiner—Eduardo C. Robert

(57) ABSTRACT

A device and a method for stabilizing cervical vertebrae in a human spine for the purpose of fixing one vertebra with respect to other vertebrae and with respect to other parts of the spinal column. This device comprises a plate and bone screws fabricated from non-metals. The bone screws maintain the plate in contact with the vertebrae. An interference fit screw head is pulled into a hole in the plate and into a machined hole in the vertebral bone, locking the screw to the plate and locking the screw to the bone. This locking reduces the screw bending within the plate and within the bone. The screw thread runout is threaded below the screw/bone interference fit area, protecting the runout stress raisers from bending and shear stresses. The interference fit is configured to create sufficient friction to eliminate the screw from backing out.

20 Claims, 3 Drawing Sheets

FIG. 5b  FIG. 5c

METHOD AND APPARATUS UTILIZING INTERFERENCE FIT SCREW SHANKS FOR NONMETALLIC SPINAL STABILIZATION

CROSS-REFERENCES TO RELATED APPLICATIONS

This patent application was preceded by Provisional Pat. No. 60/240,697 with a file date of Oct. 16, 2000.

Statement Regarding Federally Sponsored Research or Development not applicable

Reference to a Microfiche Appendix not applicable

FIELD OF THE INVENTION

The invention relates generally to implantable medical devices and their methods of use for stabilizing skeletal bone, and relates more particularly to implantable medical devices fabricated of nonmetals and their use for stabilizing the cervical vertebrae of a human spine.

BACKGROUND OF THE INVENTION

The Stabilizer Need

In normal anatomy, the vertebrae of the cervical column are held together and to the skeleton by a complex arrangement of ligaments, tendons, and muscles. Degenerative diseases, deformities, or trauma may cause abnormal conditions. These problems generally cause or allow displacement or rotation of a vertebra relative to the adjacent vertebra. When spinal discs rupture or bulge, the intervertebral space between two adjacent vertebrae 31 and 32 can decrease and cause discomfort to the patient. Frequently the bulging does no harm, but if it compresses against the spinal cord or a nerve, it may cause pain with loss of sensation, or weakness. Torn discs, torn ligaments, spinal fractures, and other conditions that affect the vertebral joints normal function can produce spinal pain. When surgery is needed, the discs are replaced with grafts that will heal or "fuse" with the vertebra. This implant, with its associated stabilization, maintains the vertebral position while healing takes place. This healing is referred to as "spinal fusion". The objective of spinal implants is to facilitate realignment and/or fixation of spinal elements. Clinical studies have demonstrated that surgeries using spinal implants are more effective at maintaining alignment and providing rigidity to the spine than surgeries in which implants are not used. Since the introduction of stabilizers as crude plates, rods, and wires; these devices have been developed into sophisticated appliances, which can be assembled and configured to rigidize spines of any size or condition. These stabilizers provide mechanical fixation for restraint of an implanted graft material. With this fixation, displacement during healing is significantly reduced thereby reducing the failure rate.

Prior Technology

The majority of existing cervical stabilizers use plates that are bent in the axial plane to conform to the vertebrae, and along the spinal axes to maintain lordosis. Bicortical screw purchase (where the screw penetrates the near side and the far side of the vertebra) has been favored because of the increased strength of the construct and increased screw thread area within the bone. These screws are more technically challenging to place and implanting them adds an increased risk of morbidity from neural canal penetration. The reduced strength and decreased thread area of a unicortical screw purchase (where the screw penetrates only the near side of the vertebra) increases the probability of screw backout or loosening which may result in esophageal injury. Screw backout and loosening has led to the development of mechanisms for locking the screw head to the plate in unicortical screw plate designs. Such locking mechanisms not only prevent screw backout, they also reduce the tendency of the screw head to pivot within the plate. These devices contain many intricate components that increase the cost and reduce reliability of stabilizer systems. The unicortical metal devices presently available are relatively rigid devices.

Nonmetal stabilizers are preferred over metallic stabilizers because of the minimal interference with X-rays and magnetic resonant imaging (MRI) techniques used for postoperative evaluation. Bendability or precurvature of the plate is also desired to accommodate or restore the natural lordosis of the cervical spine. These, and other desirable features and advantages, are provided by the present invention, particular embodiments of which are described in the Detailed Description Of The Patent section of the present patent.

Once complete fusion has taken place the plate is no longer needed. Indeed it is undesirable because it may interfere with esophageal action or may later fracture resulting in esophageal injury. A fractured bone that has been fixed with a metallic stabilizer is much more likely to refracture if the stabilizer is removed or if the stabilizer breaks. Refracture may occur because the stress sharing or stress shielding, that the metal stabilizer provided during healing, has not allowed the bone to carry sufficient load to return to normal load bearing strength. The compression forces should be gradually transferred from the stabilizer to the healing bone. Bioabsorbable and biodegradable materials will reabsorbe into the bone and provide a gradual reduction of the plate and screw material after fusion. This allows temporal load shareing, promoting bony maturation and strengthening, and will eliminate possible internal injury, a second operation, refracture, and imaging artifacts.

The following patents are examples of the complications and stress raisers in effort to prevent screw backout. These stress raisers are not suitable for use in polymeric stabilization:

U.S. Pat. No. 5,578,034 to Estes discloses a bone screw with an enlarged head and an annular collar surrounding the bone screw shaft. The collar's inner diameter shrinks in response to a change in temperature, trapping the collar between head and the threads of the bone screw.

U.S. Pat. No. 5,275,601 to Gogolewski discloses an absorbable screw where a portion of the length of the screw head has a three-dimensional structure consisting of corrugations or serrations around the outer surface of the head portion. These serrations will cause stress raisers that may create cracks during fatigue cycling and will lead to screw and plate failure.

The following patents are examples of materials which may be used in the devices of this patent:

U.S. Pat. No. 5,522,895 to Mikos discloses biodegradable and bioresorbable materials and treatments that may be used in the device of this present patent.

U.S. Pat. No. 6,269,716 to Amis discloses a tapered screw head for biodegradable medical implants. The screw head has a star shaped outer circumference with external features for rotation. In the disclosed patent the resorbable fastener tapered head is connected to a threaded shaft. The stress raisers of both the threaded portion and tapered head are in the high stressed area at the plate/bone interface. This design is successfully used in non-load bearing bones in facial and cranial surgeries. However it does not have the required strength for load bearing applications.

The following patent is an example of stabilizing systems that disclose or claim tapered screws:

U.S. Pat. No. 6,228,085 to Theken discloses metallic bone fixation system with a three-dimensionally anatomically contoured plate to fit the anterior lateral profile of the vertebrae and forming a ledge to maintain the space between two vertebrae. The system is designed for use as a metal plate and is suited for thoracic and lumbar spines. It uses setscrews and threads in a portion of the hole. It has irregular surfaces in the plate such as steps, spines or teeth to bite into a bone. The screw may have a tapered outer surface adjacent to the threaded portion to provide pullout resistance of the screw in the plate.

Polymeric Stabilizers

Polymeric stabilizers have been patented and implanted in animal spines, however none have been successful, because of material failure. Making a polymeric stabilization system that will compete with present titanium plates is a challenge. Most previous polymeric stabilization systems have been designed similar to metal plate systems. The successful utilization of these polymers requires a novel design, which will operate within the limitations of polymeric material properties. The toughest bio-compatible polymers available have a tensile strength ⅟25 that of titanium and they are 50 times more elastic than titanium. Any successful polymeric systems must be designed to operate with a minimum of stress concentrations and have the highest possible fatigue endurance limit.

Stress Concentrations

Failures in mechanical devices, including present metal spinal stabilization systems, usually initiate at sites of local stress concentration caused by geometrical or microstructure discontinuity. These stress failures are related to the type of material, the nature of the stress, the environmental conditions, and the geometry of the component at these local stresses. The local stress is raised or concentrated near the root of a notch and may be many times higher then the nominal stress, or the calculated stress of the cross section. Thread roots are especially vulnerable to high stresses for two reasons. First the groove bottom is nearly sharp, creating high stress concentrations and second the cross sectionalal area of the screw is decreased at the root, reducing the area reacting the force.

Endurance Limits

Materials can fracture at a level below the ultimate single cycle load strength, if the load is repeated a sufficient number of times. This reduced fracture strength is referred to as the endurance limit. Cyclic failures start as a point of minute local stress and progressively grows across the section until the remaining sectional area can no longer support the load and the part fractures in tension. The point of crack initiation may be as small as a scratch. Surface and internal defects such as roughness, scratches, notches, grooves, shoulders, and other abrupt changes in geometry will reduce the fatigue strength of the part.

Assuming that the average fusion patient strains the fusion five thousand times per day, and assuming that the bone will grow strong enough to support itself in 90 days, the stabilizer would require a fatigue life of 450,000 cycles. The Food and Drug Administration document "Guidance for Spinal System 510(k)" requires five million compression stress repetitions without failure Locking Tapers Locking tapers, sometimes called self locking or self-holding tapers, are tapered small angled round shanks that fit into round sockets with matching taper angles. These tapers are usually less than 5 degrees on a side. During engagement the shanks are firmly seated in the socket by an axial force such as tapping with a hammer or drawing in with a screw thread. These axial forces provide a normal force component that is sufficient to create frictional forces, which will resist relative rotation of the shank with the socket.

SUMMARY OF THE INVENTION

The present patent discloses a device and a method of implantation for stabilizing cervical vertebrae in a human spine for the purpose of temporarily fixing one vertebra with respect to other vertebrae and with respect to other parts of the spinal column. This device comprises a nonmetallic plate and bone screws fabricated from non-metals. The plate has a plurality of interference fit holes to engage the bone screws. The bone screw has a threaded portion that engages a predrilled and threaded hole in the vertebra or the graft. The bone screw also has an interference fit portion between the bone surface and the thread portion, with a diameter greater than the diameter of the hole. The bone screw maintains the plate in contact with the vertebra. The screw interference fit portion is pulled into a matching plate hole, locking the screw to the plate. The interference fit is configured to be self-locking, thus preventing the screw from backing out. The inventors have reduced this device to practice in a molded plate and machined screws fabricated from MacroPore 70:30 Poly(l-lactide-co-D,L-lactide) resorbable material. These devices have been successfully tested in accordance to FDA 510 (k) in excess of five million cycles.

OBJECTS OF THE PRESENT INVENTION

An object of the present invention is to provide a method of implanting a device for fusion, fixation and/or for spinal stabilization.

Another object of the present invention is to provide a stabilizer device, which will degrade and disappear once the bones have healed.

Another object of the present invention is to provide a spinal fusion and stabilization system using harvested bone, absorbable implants and nonmetallic stabilization plates and plate attachment devices.

Another object of the present invention is to provide devices and methods for cervical spinal fusions, anterioraly, posteriorly, and/or laterally.

BRIEF DESCRIPTION OF THE DRAWINGS

The present invention will be understood better from the following detailed description of the preferred embodiment. In the accompanying drawings the reference numbers refer to the individual parts described in the text.

FIG. 5b is an enlarged sectional view of the bone screw wrench socket in the tapered portion.

FIG. 5c is an enlarged sectional view of the bone screw with a buttress thread.

DETAILED DESCRIPTION OF THE INVENTION

For simplification the stabilizer system is described as a cervical stabilizer in one of many conceivable embodiments. That is not to imply that this is the only embodiment within which the stabilizing system can be configured. For consistency in this patent the word "stabilizer" refers to the plate-screw assembly, whereas the word "graft" refers to the material replacing the removed disc or vertebrae. This device comprises a plate and bone screws fabricated from polymeric, plastic, biodegradable, bioabsorble, resorbable, human tissue, allograft, autograft, or composite material.

The Device

Figure 1:
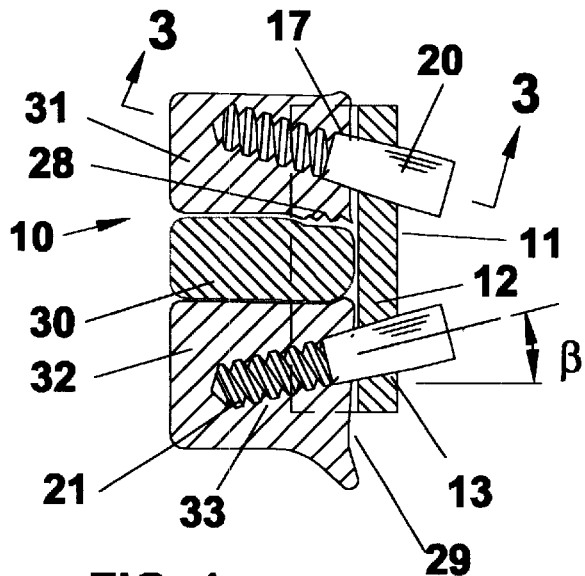
FIG. 1 is a side sectional view of the nonmetallic spinal stabilization system shown implanted on the cervical portion of a human spinal column and retaining a graft, taken along line 1—1, of FIG. 3.
Figure 2:
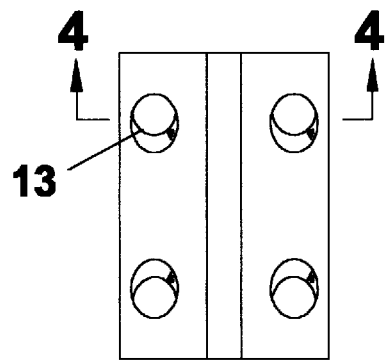
FIG. 2 is a front (anterior) view of the plate
Figure 3:
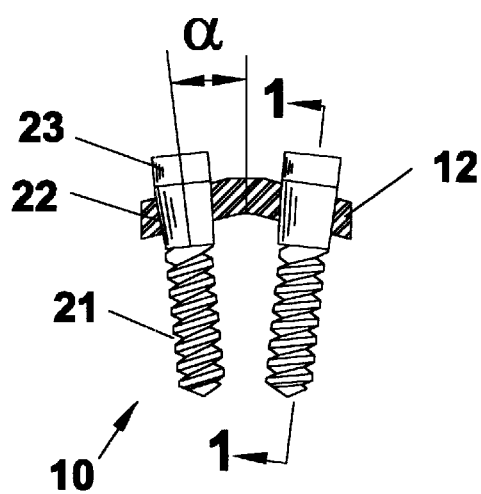
FIG. 3 is an end sectional view of the nonmetallic spinal stabilization system shown with the vertebrae removed, taken along line 3—3, of FIG. 1.

Referring to FIGS. 1, 2, and 3, in the preferred embodiment, the system is attached to the anterior surface of the spine 29. The system 10 may be modified for use on the lateral aspects of the spine. The system comprises plate 12 and bone screws 20. The system 10 and its components are described in detail in the following paragraphs. The bone stabilizing method of implanting is described in a subsequent section of this patent.

Figure 9:
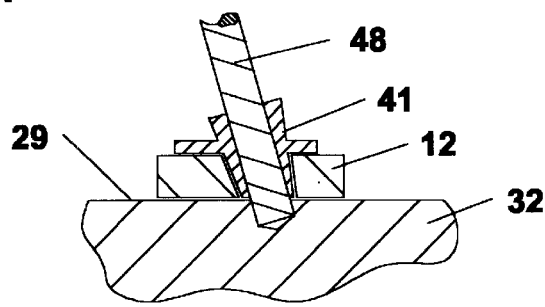
FIG. 9 is a side sectional view of a tap drill positioned with a drill guide.
Figure 10:
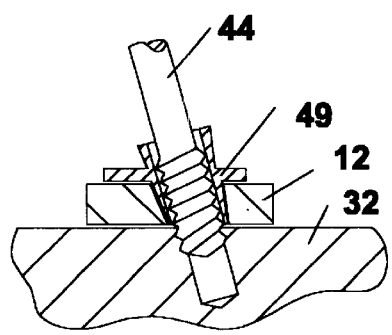
FIG. 10 is a side sectional view of a tap positioned with a tap guide.
Figure 11:
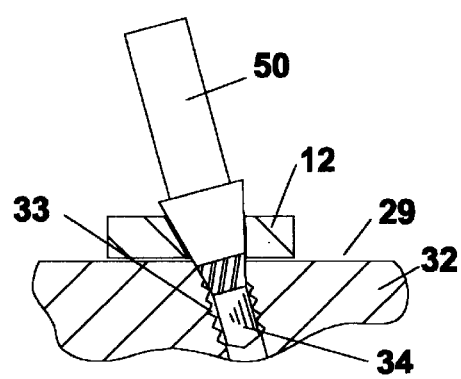
FIG. 11 is a side sectional view of a reamer guided by a pilot pin in the drilled hole.

Referring to FIGS. 1, 2, and 3, in particular, the anterior cervical plate system 10 is shown in combination with bone screws 20. Each plate 12 has interference fit holes 13 for receiving a bone screw. Bone screws 20 each include a head 23, a threaded portion 21, and a interference fit portion 22 between the head 23 and the threads 21. In the preferred embodiment, the plate holes have a minor diameter that exceeds the major diameter of the threads 21. These diameters allow the bone screws 20 to be inserted, threaded portion first, into any of screw holes 13 from the anterior side 11 of plate 12, with the threaded shank 21 passing through the hole 13 of the posterior surface. Referring to FIGS. 9, 10, and 11, the thread engages a predrilled and prethreaded hole 33 (described in the method section of this patent) in the vertebrae or the graft 30. The bone screws maintain the plate 12, in contact with the vertebrae 31 and 32. It may be necessary to remove a portion of the vertebral protrusion 28 for proper fit. The screw interference fit portion 22 is pulled into the matching plate hole 13 locking the screw 20 to the plate 12. The interference fit is configured to be self-locking preventing the screw from backing out, loosening the screw in the bone and plate.

The device is sufficiently rigid in the interfaces to reduce the lateral motion on the fusion surfaces. The area of interface is defined as the screw hole 13 in the plate, the screw interference portion 22, from the top of the plate to the screw thread run-out, and the bone hole from the surface to the thread runout. The bone screw 20 maintains an interference fit in the plate screw hole 13 and in the interference fit portion of the bone hole 17 in FIG. 1. This interference fit will decrease the bending stresses in the weakened area of the screw thread run-out. The fit will not allow the screw to bend thus replacing the high surface bending stress and its stress concentrations with a uniform shear stress at the plate bone interface. In the device of this patent there are no sharp notches or abrupt changes in the geometry of the screw head 23, the screw interference fit portion 22, nor in the plate hole surfaces 13, within the area of the greatest bending stresses.

The screw uses an interference fit, in the bone and the plate, not only to stiffen it to prevent bending, but also to prevent the screw from backing out. The screw interference is of sufficient length to extend the press fit section through the plate and into the vertebral bone hole. Clearance is eliminated between the screw interference fit portion 22 and the bone interference hole 17, shown in FIG. 1 and the plate hole 13, eliminating the associated looseness impact during each cycle. This fit provides an increased stiffness of the bone-screw-plate interfaces.

The Plate

Figure 4A:
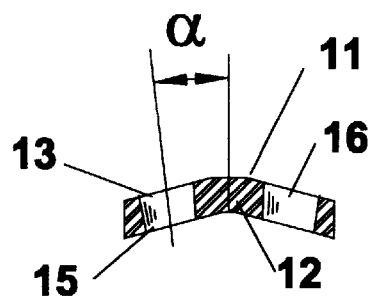
FIG. 4a is an end sectional view, of the plate with a "V" shaped posterior side, taken along line 4—4 of FIG. 2.

The plate 12, shown in FIGS. 1, 2, 3, 4a, and 4b, is the framework upon which the bone screws 20 are attached. The plate 12 has two holes 13 per vertebra to receive and contain the bone screws 20. In the preferred embodiment the plate 12 is fabricated from a single piece of material. In prior art these plates were metal and contained threads for locking the screw; or small locking devices such as cams were used to prevent the screws from backing out under repetitive movement of the patient. Most nonmetallic materials do not have the yield, tensile, compressive, endurance, or shear strengths required to support clamp screw threads. To eliminate the use of plate threads on these materials, the screw 20 is held in place with an interference fit on the screw interference fit portion 22, allowing the use of the full plate thickness for a holding area. The plate may utilize tapered holes 16, with the small diameter 15 at the posterior side of the plate as shown in FIG. 4a, mating with tapered portions, on the screws, to permit easier installation.

As an option, plate 12 may be furnished with no holes in it. In this option the plate is positioned for implanting, then the surgeon will drill pilot holes with drilling tool 48 in the plate and continue drilling into the vertebra. Using the drilled hole as a guide the surgeon will ream the hole in the plate and on into the bone in one operation as described in the optional method section of this patent.

Figure 4B:
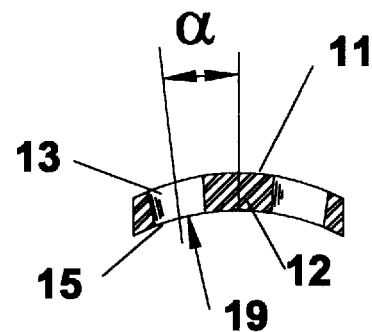
FIG. 4b is an end sectional view of FIG. 2, of the plate with a curved posterior side taken along line 4—4 of FIG. 2.
Figure 7:
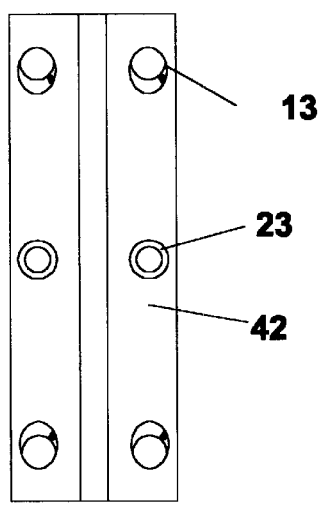
FIG. 7 is a front (proximal) view of a two level plate.
Figure 8:
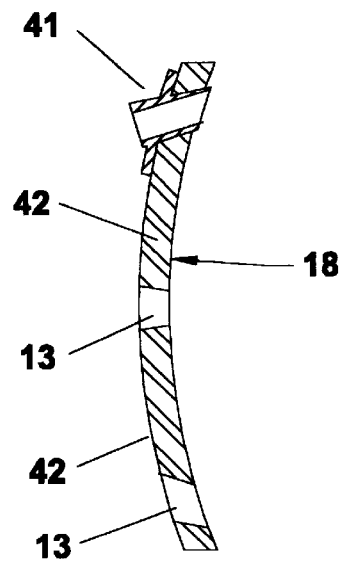
FIG. 8 is a side sectional view of a two level plate, shown in FIG. 7, with a matching lordotic curvature.

The plate may be curved or shaped to allow for stabilizing the spine or positioning individual vertebra as required. Plate 12 may contain curve 18, as shown in FIG. 8 or curve 19 as shown in FIG. 4b, such that the posterior surface of the plate is generally concave and the anterior surface 11 is generally convex. The radius of curvature in the longitudinal plane 18 is selected to match the desired lordosis of the section of the cervical vertebral column to which plate 12 is affixed. The radius of curvature in the transverse plane 19 is selected to conform to the transverse curvature of the anterior surfaces of the cervical vertebrae. The plate may be reconfigured by heating and bending. The transverse curvature may be in the form of a v-shaped bend, as illustrated in FIG. 4a or a curved surface 19 as illustrated in FIG. 4b. The plate can also be fabricated as a two level plate 42, as shown in FIG. 7 and FIG. 8, or it may be fabricated with more levels.

The Bone Screw

Figure 5A:
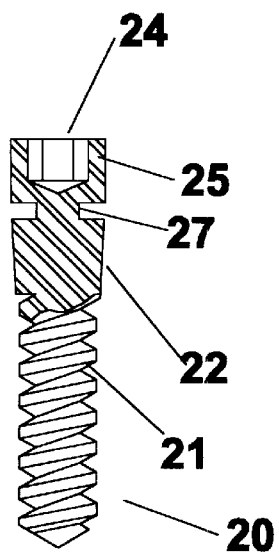
FIG. 5a is an enlarged partial section view of the bone screw, with wrench socket and a shearable head. taken along line 1—1, of FIG. 3.
Figure 5D:
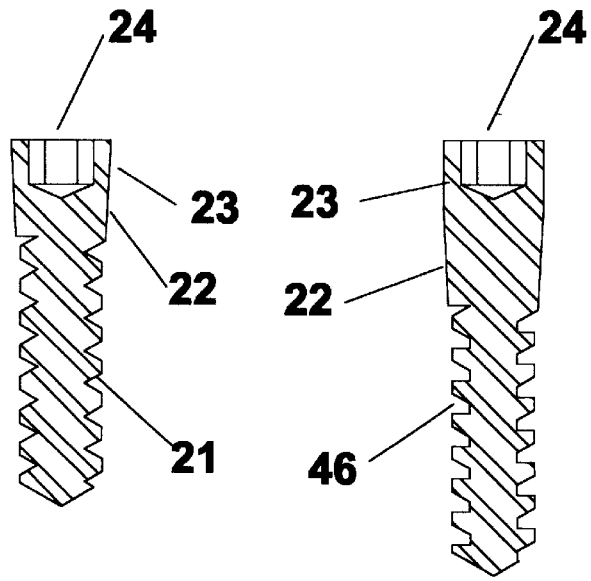
FIG. 5d is a top view of the bone screw, showing a socket head wrench fitting.
Figure 5D:
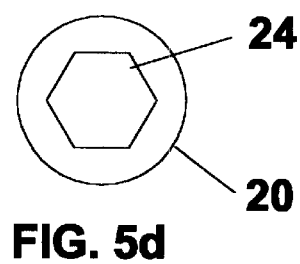
Figure 6:
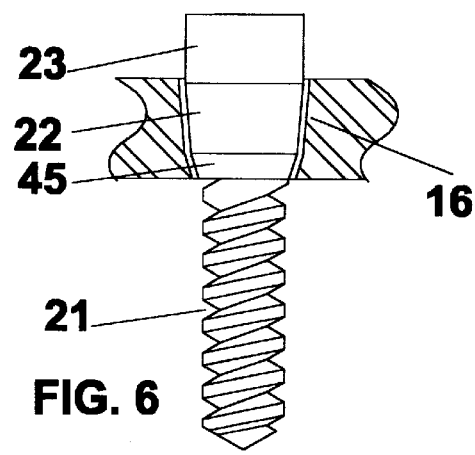
FIG. 6 is an enlarged view of a bone screw with two tapered sections.

The bone screw 20, shown in FIG. 1, may use cylindrical or tapered bone screw threads 21, on the bone end, and it has an interference fit section 22 at the unthreaded portion of the shank. A driving tool may engage a torquing feature 24, shown in FIG. 5d, which will accept a rotational driving tool. The driving portion of the screw 25 is attached to the screw head section 23 with a small stem 27, shown in FIG. 5a which will shear off when the screw torque has reached the amount required to properly seat the shank within the plate hole 13. The head breaks off to assure that the bone threads are not tightened excessively. The wrench socket is not within the interference fit section of the head and the head does not protrude into the esophagus once the stem is sheared off. FIG. 5b shows the screw with an optional tapered head 22. FIG. 5c shows an optional buttress thread 46, which allows more tension in the screw. A bone screw 20 is threaded into a drilled and tapped hole in a selected vertebra 31 to fix the plate into the position on vertebra 31 and 32. An optional screw uses a tapered interference fit portion 22 to lock the screw to the plate tapered hole 16 and the bone hole 17. The screw interference fit portion may have two different angles 22 and 45, as shown in FIG. 6.

Plate and Screw Materials

In light of the inherent disadvantages of a metal stabilizer, described in the background section of this patent, plastic biodegradable or bioabsorbable materials may alleviate many or all of these problems. This device comprises a plate and screws, which may be fabricated from polymeric, plastic, biodegradable, bio-absorbable, resorbable, human tissue, or composite material, which provides mechanical strength to bones while also providing a guide for the growth of bone tissue. Preferably, the plate is formed of biodegradable materials. Poly(L-lactic acid), poly (lactic-co-glycolic acid), and poly (glycolic acid) are approved for human use by the Food and Drug Administration. These biodegradable products either enter metabolic pathways and are thereby absorbed into the body (bioabsorbed) or are eliminated from the body by other natural processes (e.g. in the urine).

A polymeric matrix formed of a high molecular weight poly(L-lactic-acid) dispersed with a pore-creating substance formed of a low molecular weight poly(lactic acid) can be mixed to control the rate of digredation. Poly(glycolic acid) has greater mechanical strength than other materials and is suitable for replacement of load-bearing bone for implantation, and it has a biodegradation rate about four times greater than the biodegradation rate of the polymeric matrix.

LactoSorb® is an absorbable co-polymer synthesized from 82% L-Lactic acid and 18% glycolic acid. Unlike the homopolymers in common use such as 100% poly-L-lactic acid (PLLA) or 100% poly-glycolic acid (PGA), LactoSorb® copolymer is amorphous (without crystallinity), which gives it a uniform degradation rate. Crystalline release, which is associated with degrading homopolymers, have been implicated in inflammatory reactions.

LactoSorb® co-polymer ratios permit the polymer to retain most of its strength for six to eight weeks, which is appropriate for healing, but not so long as to raise concerns about long-term bone stress shielding. Mass loss, which always follows strength loss for absorbable polymers, occurs in approximately twelve months for LactoSorb® copolymer. LactoSorb® is registered trade marked material of Arthrotek® a Biomet Company.

MacroPore Inc. of San Diego manufactures a medical grade of 70:30 Poly(l-lactide-co-D,L-lactide) resorbable material. This material is FDA approved for cranial and facial applications, however it had not been successfully used on load bearing bones.

The Graft

After removing the disc and the cartilage, a graft 30, shown in FIG. 1, preferably a nondegrading bone growth-compatible material, is positioned between the two vertebra 31 and 32 in the intervertebral space. Such grafts are structurally load-bearing devices, capable of supporting the compressive forces of the adjacent superior vertebra 31. The grafts will not resist tensile forces at the vertebral to graft interface. The stabilizer 10 and the surrounding ligaments, tendons, and muscles must be preloaded to maintain compression between the graft and the adjacent vertebra until sufficient fusion occurs. The graft 30 must be in compressive contact with the vertebrae 31 and 32 to promote adequate fusion. The graft 30 may be made of metal, nonmetal, polymeric, allograft or autograft materials.

The Method

After the disc is removed, graft 30, shown in FIG. 1, is forced onto position at the center of the vertebral end plates 31 and 32. Replacing damaged discs with rigid grafts is well known to those practiced in the art. The method of stabilizing the graft and maintaining the relationship between the two vertebrae is still a changing technology. The posterior side of the plate 12 may be placed temporarily on the vertebra near the area where it will be attached and repositioned to determine the best location for the screws. Once the plate is positioned, the drill guide 41, shown in FIG. 9, is inserted into a plate hole 13 or tapered hole 16 to align the tap/pilot drill 48 with the hole centerline. After drilling the pilot hole, the tap bushing 49, shown in FIG. 10, is placed into the plate hole and the tap is rotated, threading the bone holes. After drilling and removing the bushings 41 and 49, the reamer 50, shown in FIG. 11, is inserted using a guide pin 34 guided by the drilled hole then the reamer is rotated to cut the bone hole. The tap stem may be used as the guide pin for the reamer. The bushings 41 and 49 also protect the interference-fit hole during machining. Once the hole is completely machined, a bone screw may be installed to maintain the plate position while the other holes are prepared. Once the holes are threaded, the screws 20 are threaded into the remaining holes. On frequently used plate sizes a metal template may be used to align the drill and tap. When the screws are temporally threaded into the plate and the plate is properly set, the screws are torqued until the driving portion fractures from the screw head.

The Optional Method

In this optional method, shown in the plate will be furnished with no holes in it. After placing the plate in position for implantation, the surgeon will drill pilot holes using drilling tool 48 through the plate 12 and continue drilling into the vertebra 32. Using the drilled hole as a guide the surgeon will then tap the bone hole, with tapping tool 44, either through the plate hole or the plate is temporarily removed during tapping. Tapping may be completed before the tapered hole reaming to minimize damage to the tapered surface. Referring to FIG. 11, reaming the interference fit hole 13 or tapered hole 16 in the plate 12 and the bone hole 17 can be completed in one operation. The tap stem may be used as a guide pin for reaming the interference fit hole. The pilot drill 48, as well, may serve as a guide pin for the reamer. A single drill/reamer may drill the tap hole and ream both the plate hole and the bone hole in one operation. After reaming, the surgeon will tap the threaded hole 33 into the bone. A screw may be threaded into the bone temporarily to hold the plate in position while drilling, tapping, and reaming the additional holes. Alternately, a metallic fixture may hold the plate while it is being machined.

We claim:

1. A nonmetallic stabilizing plate system, for the purpose of fixing one bone segment with respect to one or more other bone segments within a bone column said system comprising:
   (a) a nonmetallic plate member having a posterior side for fixation to individual bone segments, said plate having a plurality of attachment holes for receiving nonmetallic bone screws;
   (b) a plurality of nonmetallic bone screws configured to engage said nonmetallic plate, and to engage the bone segments, for the purpose of retaining said plate to said bone segments, and
   (c) said bone screws having a threaded portion, an interference fit portion and a head portion, the interference fit portion having at least one plate contacting surface, and the plate having at least one screw contacting surface, wherein the interference fit portion is configured and sized such that when the screw is tightened, the at least one plate contacting surface of the interference fit portion is affixed to the plate by an interference fit, wherein the interference fit produces a substantially uniform shear stress at the plate and the bone screw contacting surface.

2. The stabilizing plate system of claim 1, wherein the threaded portion of the bone screws engages threads in machined holes within the bone segments.

3. The stabilizing plate system of claim 2, wherein the interference fit portion extends over at least 1 mm into the machined holes within the bone segments.

4. The stabilizing plate system of claim 1, wherein said interference fit between said nonmetallic bone screws and said plate is provided by at least one locking tapers which prevents screw backout.

5. The stabilizing plate system of claim 1, wherein the plate holes and bone screws have at least two tapered contacting surfaces corresponding to one another to provide the interference fit therebetween.

6. The stabilizing plate system of claim 1, wherein the interference fit portion extends over at least 1 mm of said plate.

7. The stabilizing plate system of claim 1, wherein the interference fit portion includes a tapered shank portion between the head and the threaded portion.

8. The stabilizing plate system of claim 1, wherein the plate contacting surface is positioned such that the plurality of screws are engaged at a designated axial or radial angle relative to the plate.

9. The stabilizing plate system of claim 1, wherein the screws are fixed to said plate and the bone segments with an adhesive-type bonding materials.

10. The stabilizing plate system of claim 1, wherein the plate and screws are made of biodegradable, bioabsorbable or bioresorbable materials or composite non-metallic materials.

11. The stabilizing plate system of claim 10, wherein the plate and screws are made of biodegradable non-metallic materials.

12. The stabilizing plate system of claim 11, wherein the biodegradable material has a designated degradation rate.

13. The stabilizing plate system of claim 1, wherein the plate has at least two locking tapered sections, wherein the at least two locking tapered sections have differing taper angles.

14. The stabilizing plate system of claim 13, wherein the at least two locking tapered sections are configured to provide substantially the widest moment reaction distance and substantially the highest bearing compression stress between the plate and screw.

15. The stabilizing plate system of claim 1, wherein the screw head portion has a driving portion, wherein the driving portion is attached to the screw head portion by at least one member which will shear off when the screw torque has reached the amount required to properly seat the shank portion within the attachment hole.

16. The stabilizing plate system of claim 1, wherein the shape of the plate member may be reconfigured by heating and bending.

17. The stabilizing plate system of claim 1, wherein the plate member is configured as a multi-level plate.

18. The stabilizing plate system of claim 1, wherein the plate member and screws are made from the non-metallic materials having matching physical characteristics.

19. A nonmetallic stabilizing plate system, for the purpose of fixing one bone segment with respect to one or more other bone segments within a bone column, said system comprising:
   (a) a nonmetallic plate member having a posterior side for fixation to individual bone segments, selectively providing a plurality of attachment holes to said plate with desired angles for receiving nonmetallic bone screws to achieve a desired plate-screw relationship;
   (b) a plurality of nonmetallic bone screws configured to engage said nonmetallic plate, and to engage the bone segments, for the purpose of retaining said plate to said bone segments; and
   (c) said bone screws having a threaded portion, an interference fit portion and a head portion, the interference fit portion having at least one plate contacting surface, and the plate having at least one screw contacting surface, wherein the an interference fit portion is configured and sized such that when the screw is tightened, the at least one plate contacting surface is affixed to the plate by an interference fit, wherein the interference fit decreases bending stresses in the bone screws.

20. A nonmetallic stabilizing plate system, for the purpose of fixing one bone segment with respect to one or more other bone segments within a bone column, said system comprising:
   (a) a nonmetallic plate member having a posterior side for fixation to individual bone segments, said plate having a plurality of attachment holes for receiving nonmetallic bone screws, wherein the nonmetallic plate member is made of a first material;
   (b) a plurality of nonmetallic bone screws configured to engage said nonmetallic plate, and to engage the bone segments, for the purpose of retaining said plate to said bone segments, wherein the nonmetallic bone screws are made of a second material; and
   (c) said bone screws having a threaded portion, an interference fit portion and a head portion, the interference fit portion having at least one plate contacting surface, and the plate having at least one screw contacting surface, wherein the interference fit portion is configured and sized such that when the screw is tightened, the at least one plate contacting surface is affixed to the plate by an interference fit, wherein the first and second materials from which the plate and the screws are made are matched to one another such that the interference fit places the screw contacting surface in compression and substantially decreases bending stresses in the bone screws.

* * * * *